US00PP19398P2

(12) United States Plant Patent
Dumas-Quesnel

(10) Patent No.: US PP19,398 P2
(45) Date of Patent: Nov. 4, 2008

(54) ***ECHINACEA* PLANT NAMED 'NORWHINAT'**

(50) Latin Name: *Echinacea purpurea*
Varietal Denomination: Norwhinat

(75) Inventor: Monique Dumas-Quesnel, Boisbriand (CA)

(73) Assignee: Norseco Inc., Laval, Québec (CA)

( * ) Notice: Subject to any disclaimer, the term of this patent is extended or adjusted under 35 U.S.C. 154(b) by 0 days.

(21) Appl. No.: 11/807,284

(22) Filed: May 26, 2007

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV–ROM search for cultivar Norwhinat PBR 03–3557 p. 1.*

* cited by examiner

*Primary Examiner*—Annette H Para
(74) *Attorney, Agent, or Firm*—C. A. Whealy

(57) ABSTRACT

A new and distinct cultivar of *Echinacea* plant named 'Norwhinat', characterized by its upright and relatively compact plant habit; large single-type inflorescences with white-colored ray florets and orange-colored receptacle spines; strong flowering stems that hold the inflorescences upright; and good garden performance.

2 Drawing Sheets

Botanical designation: *Echinacea purpurea.*
Cultivar denomination: 'Norwhinat'.

BACKGROUND OF THE INVENTION

The present invention relates to a new and distinct cultivar of *Echinacea* plant, botanically known as *Echinacea purpurea,* and hereinafter referred to by the name 'Norwhinat'.

The new *Echinacea* is a naturally-occurring whole plant mutation of the *Echinacea purpurea* cultivar White Swan, not patented. The new *Echinacea* was discovered and selected by the Inventor as a single flowering plant from within a population of plants of the cultivar White Swan grown in a controlled outdoor nursery environment in Boisbriand, Quebec, Canada during the summer of 2000.

Asexual reproduction of the new *Echinacea* by divisions in a controlled greenhouse environment in Boisbriand, Quebec, Canada has shown that the unique features of this new *Echinacea* are stable and reproduced true to type in successive generations.

SUMMARY OF THE INVENTION

The cultivar Norwhinat has not been observed under all possible environmental conditions. The phenotype may vary somewhat with variations in environment such as temperature and light intensity, without, however, any variance in genotype.

The following traits have been repeatedly observed and are determined to be the unique characteristics of 'Norwhinat'. These characteristics in combination distinguish 'Norwhinat' as a new and distinct cultivar of *Echinacea:*

1. Upright and relatively compact plant habit.
2. Large single-type inflorescences with white-colored ray florets and orange-colored receptacle spines.

3. Strong flowering stems that hold the inflorescences upright.
4. Good garden performance.

Compared to plants of the parent, the cultivar White Swan, plants of the new *Echinacea* differ primarily in plant size as plants of the new *Echinacea* are more shorter and narrower than plants of the cultivar White Swan.

Plants of the new *Echinacea* can be compared to plants of the *Echinacea* cultivar Kim's Mophead, disclosed in U.S. Plant Pat. No. 13,560. In side-by-side comparisons conducted in Boisbriand, Quebec, Canada, plants of the new *Echinacea* differed from plants of the cultivar Kim's Mophead in the following characteristics:

1. Plants of the new *Echinacea* had larger and darker green-colored leaves than plants of the cultivar Kim's Mophead.
1 . Plants of the new *Echinacea* had larger inflorescences than plants of the cultivar Kim's Mophead.
3. Inflorescences of plants of the new *Echinacea* had more ray florets than inflorescences of plants of the cultivar Kim's Mophead.
4. Receptacle spines of plants of the new *Echinacea* had orange-colored apices whereas receptacle spines of plants of the cultivar Kim's Mophead had green-colored apices.

BRIEF DESCRIPTION OF THE PHOTOGRAPHS

The accompanying photographs illustrate the overall appearance of the new *Echinacea*. The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical flowering plant of 'Norwhinat' grown in a ground bed in an outdoor nursery.

The photograph on the second sheet are close-up views of a typical mature inflorescence (left) and immature inflorescence (right) of 'Norwhinat'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Boisbriand, Quebec, Canada during the spring and summer in an outdoor nursery and under conditions and practices which approximate those generally used in commercial *Echinacea* production. Measurements and numerical values represent averages for typical flowering plants. Plants were about three years old when the photographs and description were taken.

Botanical classification: *Echinacea purpurea* cultivar Norwhinat.

Parentage: Naturally-occurring whole plant mutation of the *Echinacea purpurea* cultivar White Swan, not patented.

Propagation:

*Type.*—Divisions.

*Time to initiate roots.*—About two to three weeks.

*Time to produce a rooted young plant.*—About one to two months.

*Root description.*—Thick; white in color.

*Rooting habit.*—Freely branching; moderately dense.

Plant description:

*Plant form/growth habit.*—Upright and relatively compact plant habit; moderate branching; terminal inflorescences held upright on strong peduncles. Vigorous growth habit.

*Plant height.*—About 64.7 cm.

*Plant diameter or spread.*—About 43.5 cm.

*Basal branches.*—Quantity per plant: About three to nine. Length: About 55 cm to 65 cm. Diameter: About 9 mm to 10 mm. Internode length: About 9 cm to 12 cm. Aspect: Upright. Strength: Strong. Texture: Moderately pubescent. Color: Close to 144A.

Foliage description:

*Arrangement.*—Alternate, simple; sessile.

*Length.*—About 15.6 cm.

*Width.*—About 5.5 cm.

*Shape.*—Lanceolate.

*Apex.*—Acute; tapering.

*Base.*—Attenuate.

*Margin.*—Serrate; serrations widely-spaced and shallow.

*Texture, upper and lower surfaces.*—Sparsely pubescent; coarse.

*Venation pattern.*—Pinnate.

*Color.*—Developing and fully expanded foliage, upper surface: Close to 147A. Developing and fully expanded foliage, lower surface: Close to 147B.

Inflorescence description:

*Appearance.*—Rotate single-type inflorescence form with ray and disc florets. Inflorescences mostly terminal; occasional axillary inflorescence development at upper leaf axils; inflorescences held upright on strong peduncles. Inflorescences persistent.

*Frangrance.*—Slight; floral, pleasant.

*Time to flower.*—Plants flower continuously from late June to early October in Boisbriand, Quebec, Canada.

*Inflorescence longevity.*—Inflorescences maintain good substance for about four weeks on the plant.

*Inflorescence bud.*—Height: About 1 cm. Diameter: About 1.5 cm to 2 cm. Shape: Globular and covered with stiff phyllaries. Color: Close to 143C.

*Inflorescence size.*—Diameter: About 11.3 cm. Depth (height): About 4 cm. Disc diameter: About 3.5 cm. Receptacle height: About 2.5 cm. Receptacle diameter: About 1.4 cm. Receptacle color: Close to 155A.

*Ray florets.*—Length: About 4.8 cm. Width: About 1.2 cm. Shape: Elongated oblong. Apex: Emarginate. Base: Attenuate; fused into a short corolla tube. Texture, upper and lower surfaces: Smooth, glabrous. Number of ray florets per inflorescence: About 20 to 21 arranged in a single whorl. Aspect: Horizontal to drooping. Color: When opening, upper surface: Close to 157C. When opening, lower surface: Close to 157A. Fully opened, upper and lower surfaces: Close to 155A.

*Disc florets.*—Shape: Tubular; apex five-pointed. Length: About 9 mm. Diameter: About 1 mm to 1.5 mm. Number of disc florets per inflorescence: About 100. Texture: Smooth, glabrous. Color: Immature: Close to 143B. Mature: Apex: Close to 141B. Mid-section: Close to 141C. Base: Close to 155A.

*Receptacle spines.*—Quantity: One per disc floret. Length: About 8 mm to 15 mm. Width: About 1 mm. Shape: Acicular. Apex: Sharply acute. Base: Tapering. Texture: Smooth, glabrous. Color: Apex: Close to 23A. Mid-section: Close to 141C. Base: Close to 155A.

*Phyllaries.*—Quantity per inflorescence: About 50 in about three or four whorls. Length: About 7 mm to 11 mm. Width: About 2 mm to 4 mm. Shape: Lanceolate. Apex: Acute. Base: Truncate. Margin: Entire. Texture, upper and lower surfaces: Pubescent. Color, upper surface: Close to 137A. Color, lower surface: Close to 143C.

*Reproductive organs.*—Androecium: Stamens per disc floret: Five. Filament lenth: About 3 mm. Filament color: Greenish white. Anther shape: Narrowly pointed. Anther length: About 2 mm. Anther color: Close to 200A. Pollen amount: Abundant. Pollen color: Golden yellow. Gynoecium: Pistil length: About 5 mm to 7 mm. Stigma shape: Bi-parted. Stigma color: Close to 144A. Style length: About 5 mm. Style color: Close to 144D. Ovary color: Close to 155D. Seeds: Length: About 4 mm. Diameter: About 1 mm. Texture: Smooth. Color: Brownish.

Disease/pest resistance: Plants of the new *Echinacea* have not been shown to be resistant to pathogens and pests common to *Echinacea*.

Temperature tolerance: Plants of the new *Echinacea* have been observed to tolerate temperatures from about −15° C. to about 35° C.

It is claimed:

1. A new and distinct *Echinacea* plant named 'Norwhinat' as illustrated and described.

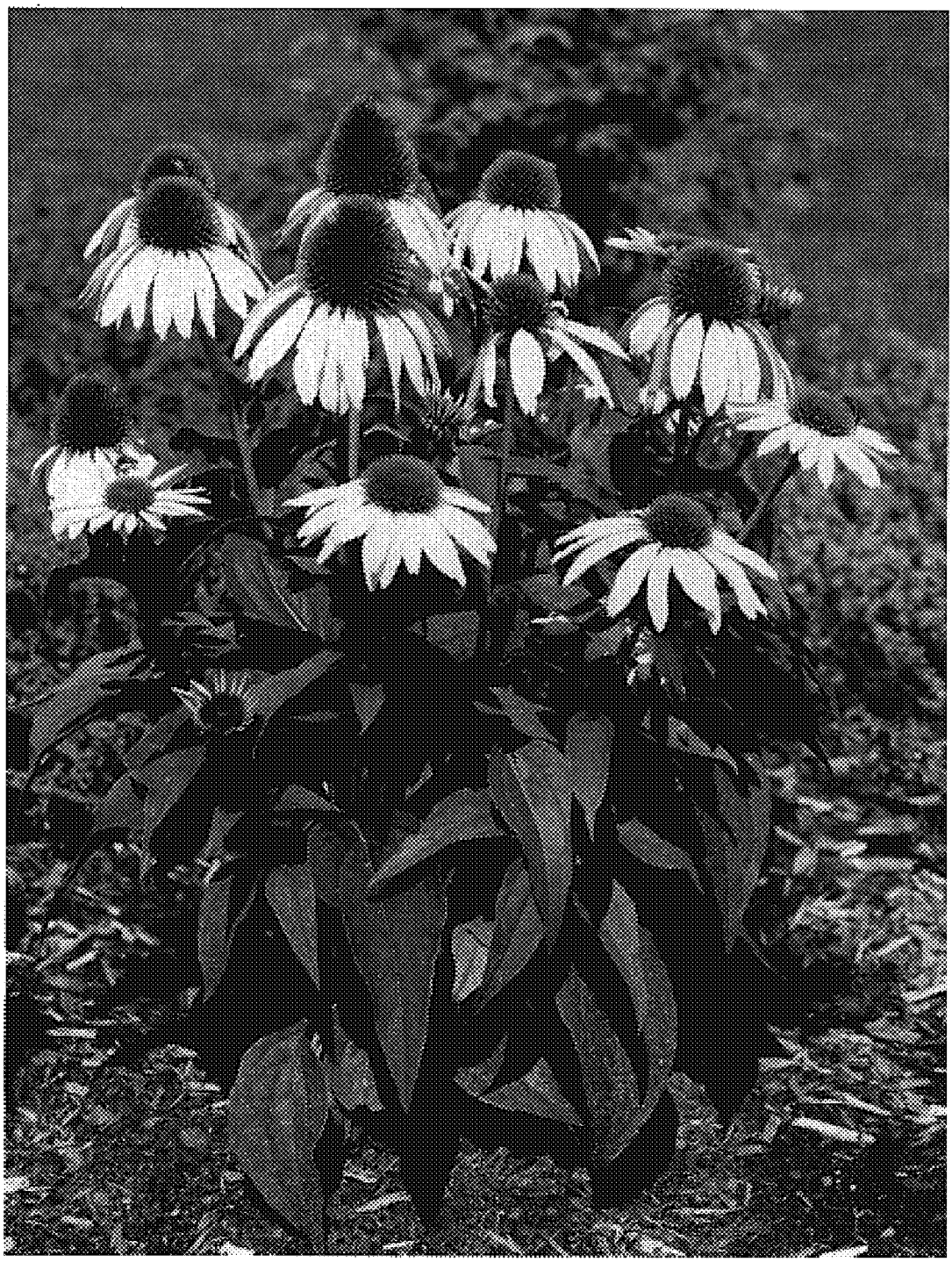

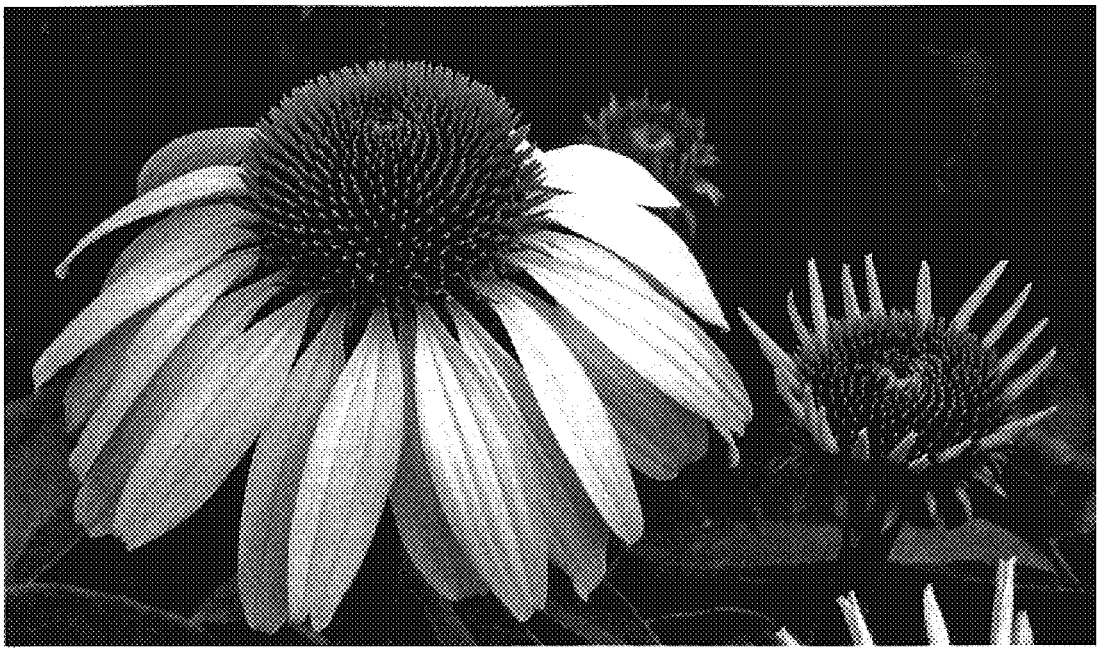

* * * * *